US008273885B2

(12) United States Patent
Tanaka et al.

(10) Patent No.: US 8,273,885 B2
(45) Date of Patent: Sep. 25, 2012

(54) FLUOROBORON COMPOUND HAVING AROMATIC RING OR SALT THEREOF, AND METHOD FOR PRODUCING COMPOUND HAVING CYCLIC ETHER-FUSED AROMATIC RING USING THE SAME

(75) Inventors: Keigo Tanaka, Tsukuba (JP); Norio Murai, Tsukuba (JP); Shuji Shirotori, Tsukuba (JP); Satoshi Nagao, Tsukuba (JP); Yuzo Watanabe, Tsukuba (JP)

(73) Assignee: Eisai R&D Management Co., Ltd., Tokyo (JP)

(*) Notice: Subject to any disclaimer, the term of this patent is extended or adjusted under 35 U.S.C. 154(b) by 368 days.

(21) Appl. No.: 12/440,557

(22) PCT Filed: Sep. 11, 2007

(86) PCT No.: PCT/JP2007/067652
§ 371 (c)(1),
(2), (4) Date: Mar. 9, 2009

(87) PCT Pub. No.: WO2008/032702
PCT Pub. Date: Mar. 20, 2008

(65) Prior Publication Data
US 2010/0056788 A1 Mar. 4, 2010

(30) Foreign Application Priority Data
Sep. 11, 2006 (JP) .................................. 2006-245837

(51) Int. Cl.
*C07F 5/02* (2006.01)
(52) U.S. Cl. .............................................. 546/13; 568/6
(58) Field of Classification Search .................... 546/13, 546/89, 115; 549/469; 556/7; 568/6
See application file for complete search history.

(56) References Cited

U.S. PATENT DOCUMENTS
2008/0242859 A1 10/2008 Tanaka et al.

OTHER PUBLICATIONS

Molander et al. Organic Letters 2006, 13(8), Supporting Information, pp. S12-S13.*
J. Mar., Advanced Organic Chemistry: Reactions, Mechanisms, and Structure (4th Ed. 1992), p. 1470.*
Thomas L. Gilchrist, Heterocyclic Chemistry (3rd ed. 1992), Chapter 2: pp. 8-37.*
Kosugi et al., "Novel Hyroxymethylation of Aryl Bromides by Means of Organotin Reagents", Chemistry Letters, pp. 997-998, 1985.
Extended European Search Report dated Oct. 10, 2011 for the European Application No. 07807061.2.
Unterhalt et al., "Neue Substituierte Isochromane," Pharmazie, vol. 51, No. 9, Jan. 1, 1996, pp. 641-644, XP008142697.
Response to the European Office Action dated Apr. 24, 2012, for Application No. 07807061.2.
International Search Report and Written Opinion of the International Searching Authority for Appl. No. PCT/JP2007/067652 dated Oct. 9, 2007 (w/ English translation of Written Opinion).
JPO International Search Report for Appl. No. PCT/JP2007/067652 dated Oct. 9, 2007.
Molander, G. A. et al, "B-Alkyl Suzuki-Miyaura Cross-Coupling Reactions with Air-Stable Potassium Alkyltrifluoroborates," J. Org, Chem., 2003, vol. 68, No. 14, pp. 5534-5539.
Molander, G. A. et al, "Cross-Coupling Reactions of Potassium Alkyltrifluoroborates with Aryl and 1-Alkenyl Trifluoromethanesulfonates," Organic Letters, 2001, vol. 3, No. 3, pp. 393-396.
Molander, G.A. et al, "Palladium-Catalyzed Suzuki-Miyaura Cross-Coupling Reactions of Potassium Aryl- and Heteroaryltrifluoroborates," J. Org. Chem, 2003, vol. 68, No. 11, pp. 4302-4314.
Unterhalt, B. et al, "Neue Substituierte Isochromane," Pharmazie, Jan. 1, 1996, vol. 51, No. 9, pp. 641-644 (w/ English translation), XP 008142697.
Kosugi et al., "Novel Hydroxymethylation of Aryl Bromides by Means of Organotin Reagents", Chemistry Letters, pp. 997-998, 1985.

* cited by examiner

*Primary Examiner* — Jason M Nolan
(74) *Attorney, Agent, or Firm* — Birch, Stewart, Kolasch & Birch, LLP

(57) ABSTRACT

Provided is a fluoroboron compound which is highly safe and stable and is capable of forming a cyclic ether-fused ring by the intramolecular alkoxymethylation reaction, or a salt thereof. The compound can be synthesized by the intramolecular alkoxymethylation reaction of a fluoroboron compound represented by the formula (I) or a salt thereof in the presence of a metal catalyst.

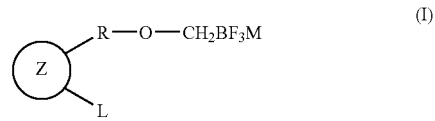

(I)

(wherein the moiety represented by the formula

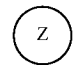

represents an aromatic ring; L represents a substituent such as a halogen atom; R represents a substituted or unsubstituted alkylene group having 1 or 2 carbon atoms; and M represents an alkali metal cation or the like, with the proviso that L and —R—OCH$_2$BF$_3$M are respectively located on contiguous carbon atoms on the aromatic ring, or in the case of a fused aromatic ring, on two carbon atoms adjacent to one carbon at the fused position).

9 Claims, No Drawings

FLUOROBORON COMPOUND HAVING AROMATIC RING OR SALT THEREOF, AND METHOD FOR PRODUCING COMPOUND HAVING CYCLIC ETHER-FUSED AROMATIC RING USING THE SAME

BACKGROUND OF THE INVENTION

1. Field of the Invention

The present invention relates to a fluoroboron compound or a salt thereof from which a cyclic ether fused with an aromatic ring can be formed by an intramolecular alkoxymethylation reaction, a production method thereof, and a method for synthesizing a compound having a cyclic ether-fused aromatic ring using the fluoroboron compound or the salt thereof.

2. Description of the Related Art

To date, there have been reports on intermolecular coupling reactions in which an oxymethyl group, such as an alkoxymethyl group or a hydroxymethyl group, is introduced in an aromatic ring by the use of an organotin compound, such as an alkoxymethyl tin compound, in the presence of a palladium catalyst. As the organotin compounds which can be used in this reaction, methoxymethyltributyltin disclosed in Non-patent Document 1, hydroxymethyltributyltin disclosed in Non-patent Document 2, and the like have been reported. In addition, an alkoxymethylfluoroboron compound is disclosed in Non-patent Documents 3 and 4.

[Non-patent Document 1] Chem. Lett., 1225, 1984.
[Non-patent Document 2] Chem. Lett., 997, 1985.
[Non-patent Document 3] Org. Lett., 8, 2031, 2006.
[Non-patent Document 4] Org. Lett., 8, 2767, 2006.

The organotin compounds disclosed in the abovementioned Non-patent Documents 1 and 2 are known as reagents that can alkoxymethylate or hydroxymethylate (hereinafter these processes are collectively referred to as "oxymethylation") the aromatic ring in the presence of a metal catalyst. However, the toxicity of these organotin compounds may cause problems, and thus they are not suited for industrial use. Moreover, the organotin compounds are not suited for large industrial scale production since the production requires purification by chromatography using silica gel in many cases. For this reason, the development of compounds to be used in the metal catalyzed oxymethylation reaction of aromatic rings which are excellent in terms of safety and which can also be easily produced on a large scale and the establishment of a method for producing such compounds have been desired. Organoboron compounds are highly safe as compared to organotin compounds. Moreover, it is known that the organic fluoroboron compounds generally have excellent stability and are also easy to handle. However, there is no known example of using the oxymethyl fluoroboron compounds disclosed in the abovementioned Non-patent Documents 3 and 4 for the intermolecular oxymethylation of aromatic rings.

Furthermore, in addition to the abovementioned problems, the alkoxymethylation reaction described above is limited to the intermolecular reaction, and no method is known to date for synthesizing a compound having a cyclic ether-fused aromatic ring by the intramolecular alkoxymethylation reaction in the presence of a metal catalyst.

SUMMARY OF THE INVENTION

An object of the present invention is to provide a method for producing a compound having a cyclic ether-fused aromatic ring through the intramolecular alkoxymethylation reaction of an aromatic compound by the use of an organic fluoroboron compound or a salt thereof which is highly safe and stable and is also easy to handle; a compound to be used in the method; and a method for synthesizing the compound.

The present inventors discovered that it is possible to form a cyclic ether fused with an aromatic ring through the intramolecular alkoxymethylation reaction by the use of a fluoroboron compound or a salt thereof, thereby completing the present invention.

The fluoroboron compound or the salt thereof according to the present invention is a fluoroboron compound having an aromatic ring or the salt thereof, and is a fluoroboron compound which is capable of forming a cyclic ether fused with the aromatic ring or the salt thereof by the intramolecular alkoxymethylation reaction.

Moreover, the fluoroboron compound or the salt thereof according to the present invention is preferably a fluoroboron compound which is represented by the following formula (I) or a salt thereof.

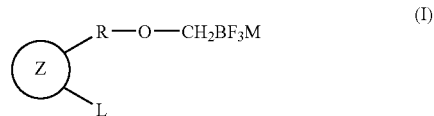

(in formula (I), the following moiety:

represents an aromatic ring which may or may not have substituents other than L and —R—O—CH$_2$BF$_3$M groups; L represents a leaving group; R represents a substituted or unsubstituted alkylene group of 1 or 2 carbon atoms; M represents an alkali metal cation, [N(R$^1$)(R$^2$)(R$^3$)(R$^4$)]$^+$, or [P(R$^1$)(R$^2$)(R$^3$)(R$^4$)]$^+$, wherein R$^1$, R$^2$, R$^3$, and R$^4$ each independently represents a C$_{1-6}$ alkyl group or a C$_{7-16}$ aralkyl group; with the proviso that L and —R—OCH$_2$BF$_3$M are respectively located on contiguous carbon atoms on the aromatic ring or, in the case of a fused aromatic ring, on two carbon atoms adjacent to one carbon at the fused position).

The leaving group L is preferably a group selected from the group consisting of a halogen atom, a substituted or unsubstituted alkylsulfonyloxy group, and a substituted or unsubstituted arylsulfonyloxy group, more preferably a halogen atom, and particularly preferably a chlorine atom or a bromine atom.

Moreover, in the formula (I) above, R preferably represents a methylene group or an ethylene group which may optionally be substituted by one or more C$_{1-6}$ alkyl groups, and it is particularly desirable that R represents an unsubstituted methylene group or an unsubstituted ethylene group.

Furthermore, in the formula (I) above, the aromatic ring represented by the following moiety is preferably selected from the group consisting of a benzene ring, a naphthalene ring, an anthracene ring, a furan ring, a thiophene ring, a pyrrole ring, an imidazole ring, a triazole ring, a thiazole ring, a pyrazole ring, an oxazole ring, an isoxazole ring, an isothiazole ring, a furazan ring, a thiadiazole ring, an oxadiazole ring, a pyridine ring, a pyrazine ring, a pyridazine ring, a pyrimidine ring, a pteridine ring, a quinoline ring, an isoquinoline ring, a naphthyridine ring, a quinoxaline ring, a cinnoline ring, a quinazoline ring, a phthalazine ring, an imidazopyridine ring, a benzothiazole ring, a benzoxazole ring, a benzimidazole ring, an indole ring, an isoindole ring, an indazole ring, a pyrrolopyridine ring, a thienopyridine ring, a furopyridine ring, a benzothiadiazole ring, a benzoxadiazole ring, a pyridopyrimidine ring, a benzofuran ring, a benzothiophene ring, a benzo[1,3]dioxole ring, and a thienofuran ring.

Moreover, in the formula (I) above, the aromatic ring represented by the following moiety:

is preferably selected from the group consisting of a benzene ring, a naphthalene ring, a pyridine ring, a pyrazine ring, a pyridazine ring, a pyrimidine ring, and a quinoline ring.

Furthermore, in the formula (I) above, the aromatic ring represented by the following moiety:

is preferably a benezene ring, a quinoline ring, or a naphthalene ring.

Note that each of the abovementioned aromatic rings may optionally have an additional substituent other than the L and —R—OCH$_2$BF$_3$M groups as described above, and those fluoroboron compounds having an aromatic ring with the substituent or the salts thereof are also included in the scope of the present invention.

Moreover, in the formula (I) above, M preferably represents an alkali metal cation, and more preferably a potassium ion or a sodium ion.

The present invention further provides a method for producing a compound represented by the following formula (II):

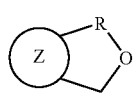

and having a cyclic ether-fused aromatic ring, and the production method of the present invention includes a step for causing an intramolecular alkoxymethylation reaction of the aforementioned fluoroboron compound or the salt thereof in the presence of a metal catalyst.

It should be noted that the fluoroboron compound of the present invention or the salt thereof may be a solvate, and thus the solvates are also one form of the fluoroboron compound of the present invention or the salt thereof and are within the scope of the present invention.

The fluoroboron compound of the present invention or the salt thereof is easy to handle and is also highly safe and stable, and a compound having a cyclic ether-fused aromatic ring can be produced by one-step reaction due to the intramolecular alkoxymethylation reaction using a metal catalyst.

DETAILED DESCRIPTION OF THE INVENTION

The terms used in the present description will be explained below.

In the present invention, the term "aromatic ring" refers to a cyclic group having aromaticity, and the aromatic ring may be a monocyclicl or a fused ring and may be an aromatic hydrocarbon cyclic group (aryl group) or an aromatic heterocyclic group (heteroaryl group), and may also include any of these with an additional substituent.

When the aromatic ring above has an additional substituent, the following may be exemplified as the substituent, although the substituent is not limited to these examples: a halogen atom (such as a fluorine atom, a chlorine atom, a bromine atom, and an iodine atom); an alkyl group which may have a hydroxyl group or an alkoxy group (such as a $C_{1-6}$ alkyl group); an alkenyl group (such as a $C_{2-6}$ alkenyl group); an alkynyl group (such as a $C_{2-6}$ alkynyl group); a cycloalkyl group (such as a $C_{3-8}$ cycloalkyl group); an aryl group (such as a phenyl group and a naphthyl group); a heteroaryl group; an aralkyl group; a heteroaralkyl group; a saturated or unsaturated non-aromatic heterocyclyl group (such as a 2-, 3-, or 4-morpholinyl group, a 2-, or 3-piperidyl group, a 2-, or 3-pyrrolidinyl group, and a 2-, or 3-tetrahydrofuryl group); a hydroxyl group; an alkoxy group (such as a $C_{1-6}$ alkoxy group); a cycloalkyloxy group (such as a $C_{3-8}$ cycloalkyloxy group); an aryloxy group; a heteroaryloxy group; a saturated or unsaturated non-aromatic heterocyclyloxy group; a carboxyl group; an alkoxycarbonyl group (such as a methoxycarbonyl group, an ethoxycarbonyl group, a propoxycarbonyl group, and a butoxycarbonyl group); a $C_{3-8}$ cycloalkyloxycarbonyl group (such as a cyclopropyloxycarbonyl group and a cyclohexyloxycarbonyl group); an aryloxycarbonyl group (such as a phenyloxycarbonyl group); a heteroaryloxycarbonyl group; a heteroaralkyloxycarbonyl group; a saturated or unsaturated non-aromatic heterocyclyloxycarbonyl group; an alkylcarbonyl group (such as a $C_{1-6}$ alkylcarbonyl group including an acetyl group, a propionyl group, and a butyryl group); a saturated or unsaturated non-aromatic heterocyclylcarbonyl group; an alkoxy-, alkenyloxy-, alkynyloxy-, cycloalkyloxy-, cycloalkenyloxy-, aryloxy-, heteroaryloxy-, aralkyloxy-, heteroaralkyloxy-, and saturated or unsaturated non-aromatic heterocyclyloxy-carbonylamino group; an alkylthio-, alkenylthio-, alkylnylthio-, cycloalkylthio-, cycloalkenylthio-, arylthio-, heteroarylthio-, aralkylthio-, heteroaralkylthio-, and saturated or unsaturated non-aromatic heterocyclylthio-carbonylamino group; an alkyl-, alkenyl-, alkynyl-, cycloalkyl-, cycloalkenyl-, aryl-, heteroaryl-, aralkyl-, heteroaralkyl-, and saturated or unsaturated non-aromatic heterocyclyl-urea group; an amino group which may have one or two types of substituents selected from the group consisting of an alkyl group, an alkenyl group, an alkynyl group, a cycloalkyl group, a cycloalkenyl group, an aryl group, a heteroaryl group, an aralkyl group, a heteroaralkyl group, and a saturated or unsaturated non-aromatic heterocyclyl group, and may be monosubstituted or disubstituted when having one type of the above substituents (wherein 2 alkyl or alkenyl groups bonded to a nitrogen atom may form a ring together which may have one or more hetero atoms); an aminocarbonyl group which may have one or two types of substituents selected from the group consisting of an alkyl group, an alkenyl group, an alkynyl group, a cycloalkyl group, a cycloalkenyl group, an aryl group, a heteroaryl group, an aralkyl group, a heteroaralkyl group, and a saturated or unsaturated non-aromatic heterocyclyl group, and may be monosubstituted or disubstituted when having one type of the above substituents; a nitro group; a cyano group;

an alkylthio group; an alkenylthio group; a cycloalkylthio group; a cycloalkenylthio group; an arylthio group; a heteroarylthio group; an alkyl-, alkenyl-, cycloalkyl-, cycloalkenyl-, aryl-, heteroaryl-, and saturated or unsaturated non-aromatic heterocyclyl-sulfonyl group.

Note that the above substituents located on the aromatic ring may have an additional substituent. In addition, the 2 alkyl substituents bonded to the adjacent carbon atoms on the aromatic ring may form a saturated or unsaturated ring together, and this ring may further include one or more hetero atoms and may also include an additional substituent. The number of substituents located on the aromatic ring is not particularly limited, and the aromatic ring may have two or more substituents of the same or different types. In these cases, the abovementioned substituents may be exemplified as the substituent, although the substituent is not limited to these.

Among the abovementioned substituents, the substituents, such as a hydroxyl group and an amino group which are capable of being protected by a protecting group, may be protected by a known protecting group. Examples of the protecting groups for an amino group include a tert-butoxycarbonyl group and a benzyloxycarbonyl group, and examples of the protecting groups for a hydroxyl group include an acetyl group, a benzyl group, a tert-butyldimethylsilyl group, and a trimethylsilyl group, although the protecting groups are not limited to these.

In the present description, the term "$C_{1-6}$ alkyl group" refers to a linear or branched monoalkyl group of 1 to 6 carbon atoms which is derived from an aliphatic hydrocarbon of 1 to 6 carbon atoms by removing any one of the hydrogen atoms therefrom. Examples of the $C_{1-6}$ alkyl groups include a methyl group, an ethyl group, a 1-propyl group, a 2-propyl group, a 2-methyl-1-propyl group, a 2-methyl-2-propyl group, a 1-butyl group, a 2-butyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, and a 2,3-dimethyl-2-butyl group. Of these, the $C_{1-6}$ alkyl group is preferably a methyl group, an ethyl group, a 1-propyl group, a 2-propyl group, a 2-methyl-1-propyl group, a 2-methyl-2-propyl group, a 1-butyl group, or a 2-butyl group, and more preferably a methyl group or an ethyl group.

In the present description, the term "$C_{1-6}$ alkoxy group" refers to an alkyloxy group in which an oxygen atom is bonded to the abovementioned $C_{1-6}$ alkyl group, and examples thereof include a methoxy group, an ethoxy group, a 1-propyloxy group, a 2-propyloxy group, a 2-methyl-1-propyloxy group, a 2-methyl-2-propyloxy group, a 1-butyloxy group, and a 2-butyloxy group, although the $C_{1-6}$ alkoxy group is not limited to these.

In the present description, the term "cycloalkyl group" refers to a saturated hydrocarbon group having a cyclic chemical structure formed of 3 or more carbon atoms. The number of carbon atoms constituting the cycloalkyl group is not particularly limited as long as it is 3 or more. However, 3 to 12 carbon atoms are preferable and 3 to 8 carbon atoms are more preferable. Specific examples of the cycloalkyl groups include a cyclopropyl group, a cyclobutyl group, a cyclopentyl group, a cyclohexyl group, and a decahydronaphthalene group.

In the present description, the term "aralkyl group" refers to a group in which an aryl group is bonded to an alkyl group. The term "$C_{7-16}$ aralkyl group", among the aralkyl groups, refers to a functional group in which the abovementioned $C_{1-6}$ alkyl group is bonded with a $C_{6-14}$ aryl group (which refers to an aromatic hydrocarbon cyclic group of 6 to 14 carbon atoms and specific examples thereof include a phenyl group, a 1-naphthyl group, a 2-naphthyl group, an indenyl group, an azulenyl group, a heptalenyl group, an indacenyl group, a biphenylenyl group, an acenaphthylenyl group, a fluorenyl group, a phenalenyl group, a phenanthrenyl group, and an anthracenyl group). Examples of the $C_{7-16}$ aralkyl group include a benzyl group, an α-naphthylmethyl group, a β-naphthylmethyl group, an indenylmethyl group, a 1-phenethyl group, a 2-phenethyl group, a 1-naphthylethyl group, a 2-naphthylethyl group, a 1-phenylpropyl group, a 2-phenylpropyl group, a 3-phenylpropyl group, a 1-naphthylpropyl group, a 2-naphthylpropyl group, a 3-naphthylpropyl group, a 1-phenylbutyl group, a 2-phenylbutyl group, a 3-phenylbutyl group, a 4-phenylbutyl group, a 1-naphthylbutyl group, a 2-naphthylbutyl group, a 3-naphthylbutyl group, a 4-naphthylbutyl group, a 1-phenylpentyl group, a 2-phenylpentyl group, a 3-phenylpentyl group, a 4-phenylpentyl group, a 5-phenylpentyl group, a 1-naphthylpentyl group, a 2-naphthylpentyl group, a 3-naphthylpentyl group, a 4-naphthylpentyl group, a 5-naphthylpentyl group, a 1-phenylhexyl group, a 2-phenylhexyl group, a 3-phenylhexyl group, a 4-phenylhexyl group, a 5-phenylhexyl group, a 6-phenylhexyl group, a 1-naphthylhexyl group, a 2-naphthylhexyl group, a 3-naphthylhexyl group, a 4-naphthylhexyl group, a 5-naphthylhexyl group, and a 6-naphthylhexyl group. Of these, the $C_{7-16}$ aralkyl group is preferably a benzyl group, a 1-phenethyl group, or a 2-phenethyl group.

In the present description, the term "heteroaryl group" refers to a heteroaromatic cyclic group having 1 or more hetero atoms. Examples of the hetero atoms include an oxygen atom, a nitrogen atom, and a sulfur atom. The heteroaryl group is preferably formed of 5 to 14 atoms in total of the hetero atoms and carbon atoms, and more preferably formed of 5 or 6 atoms. Specific examples of the heteroaryl group include a furyl group, a thienyl group, a pyrrolyl group, an imidazolyl group, a triazolyl group, a tetrazolyl group, a thiazolyl group, a pyrazolyl group, an oxazolyl group, an isoxazolyl group, an isothiazolyl group, a furazanyl group, a thiadiazolyl group, an oxadiazolyl group, a pyridyl group, a pyrazyl group, a pyridazinyl group, a pyrimidinyl group, a triazinyl group, a purinyl group, a pteridinyl group, a quinolyl group, an isoquinolyl group, a naphthylidinyl group, a quinoxalinyl group, a cinnolinyl group, a quinazolinyl group, a phthalazinyl group, an imidazopyridyl group, an imidazothiazolyl group, an imidazoxazolyl group, a benzothiazolyl group, a benzoxazolyl group, a benzimidazolyl group, an indolyl group, an isoindolyl group, an indazolyl group, a pyrrolopyridyl group, a thienopyridyl group, a furopyridyl group, a benzothiadiazolyl group, a benzoxadiazolyl group, a pyridopyrimidinyl group, a benzofuryl group, a benzothienyl group, a benzo[1,3]dioxolyl group, and a thienofuryl group, although the heteroaryl group is not limited to these.

In the present description, the term "heteroaralkyl group" refers to a group in which the abovementioned heteroaryl group is bonded to an alkyl group, for example, the abovementioned $C_{1-6}$ alkyl group.

In the present description, the term "saturated or unsaturated non-aromatic heterocyclyl group" refers to a saturated or unsaturated non-aromatic heterocyclic group, and examples thereof include a 2-, 3-, or 4-morpholinyl group, a 2-, or 3-piperidyl group, a 2-, or 3-pyrrolidinyl group, and a 2-, or 3-tetrahydrofuryl group.

As an "alkylsulfonyloxy group", a methanesulfonyloxy group and an ethanesulfonyloxy group may be exemplified, although the alkylsulfonyloxy group is not limited to these. The alkylsulfonyloxy group may have one or more substituents, and examples of the substituents include a halogen atom (particularly a fluorine atom), although the substituents are not limited to these. Preferable examples of the alkylsulfonyloxy group having a substituent include a trifluoromethanesulfonyloxy group.

As an "arylsulfonyloxy group", a benzenesulfonyloxy group may be exemplified, although the arylsulfonyloxy group is not limited to these. The arylsulfonyloxy group may have a substituent, and examples of the substituent include a halogen atom and an alkyl group (preferably a $C_{1-6}$ alkyl group), although the substituent is not limited to these. As the arylsulfonyloxy group having a substituent, a p-toluenesulfonyloxy group may be exemplified, although the arylsulfonyloxy group is not limited to these.

In the present description, the term "alkylene group" refers to a bifunctional saturated hydrocarbon group such as a methylene group and an ethylene group. The alkylene group may have an additional substituent, and examples of the substituent include an alkyl group (particularly preferably a $C_{1-6}$ alkyl group), although the substituent is not limited to these.

In the present description, the "carbon at the fused position" of the fused ring in which 2 or more aromatic rings are fused refers to a carbon atom shared by 2 aromatic rings. For example, in a naphthalene ring, the carbons at the fused positions are the carbon atoms at the 4a-position and the 8a-position. Accordingly, in the case of a naphthalene ring, the 2 carbon atoms adjacent to one carbon atom at the fused position are, for example, the carbon atoms at the 4 and 5 positions.

In the present description, the phrase "substituted or unsubstituted" means that a substituent group may optionally be contained.

In the present description, the term "solvate" refers to a solvate formed of a fluoroboron compound of the present invention or a salt thereof and a solvent. There is no particular limitation on the type of a solvent constituting a solvate and the molar ratio of a solvent to a fluoroboron compound or a salt thereof in a solvate.

Preferable examples of the solvate include a hydrate, an alcoholate (such as a methanolate, an ethanolate, a propanolate, and an isopropanolate), an ester adduct (such as an ethyl acetate adduct), an ether adduct (such as methyl etherate, ethyl etherate, and a tetrahydrofuran adduct), and a dimethylformamide adduct, and it is particularly desirable that the solvent be a hydrate or an alcoholate (such as a methanolate and an ethanolate). Also, a solvate constituting a solvate is preferably a pharmacologically allowable solvent.

In the present description, the term "alkali metal" refers to a metal atom which belongs to Group I of the periodic table, and examples thereof include lithium, sodium, and potassium, and sodium and potassium are preferable.

In the present description, the term "metal catalyst" refers to a metal and a metal-containing compound which are effective to accelerate an intramolecular alkoxymethylation reaction using the fluoroboron compound of the present invention or the salt thereof. A metal catalyst is not particularly limited, and any of the metal catalysts can be used as long as it can accelerate the aforementioned reaction. The metal catalyst is preferably a palladium catalyst.

[Production Method of Fluoroboron Compound]

A method for producing a fluoroboron compound represented by the formula (I) will be described. It should be noted that in the following description, the term "an outer temperature" refers to an outer temperature of a reaction vessel, for example, a flask.

A fluoroboron compound represented by the formula (I) can be produced, for example, by using a method represented by the reaction scheme 1 described below. However, a production method of the fluoroboron compound of the present invention is not limited to this method.

Reaction scheme 1

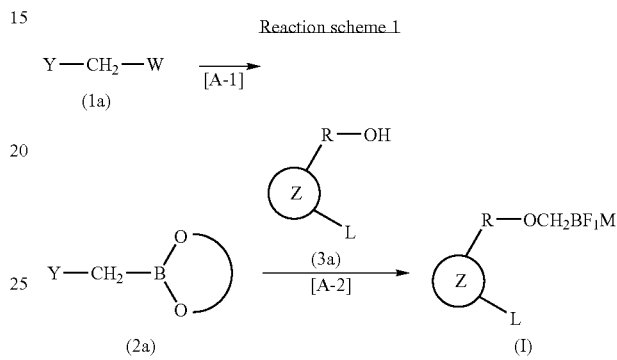

In the reaction scheme 1, the following moiety, L, R, and M each represents the same as defined above in the formula (I). Y and W each independently represents a halogen atom.

As a cyclic boronic ester group represented by the following formula X, which is a part of the abovementioned formula (2a), cyclic boronic ester groups represented by the following formula X-1 to X-6 are exemplified, although a cyclic boronic ester group represented by the formula X is not limited to these.

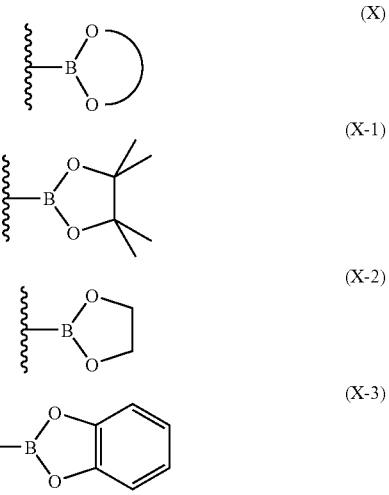

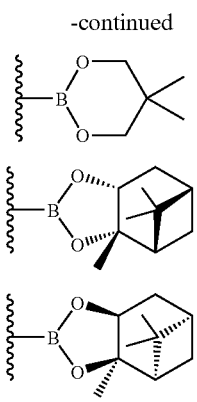

A method for synthesizing a compound represented by the formula (I), which is represented by the abovementioned reaction scheme 1, includes 2 steps composed of the step [A-1] and the step [A-2] described below.

[Step [A-1]]

The step [A-1] is a step that includes, for example, reacting an anionized compound, which is produced by the reaction of a compound (1a) and an organometallic reagent selected from n-butyl lithium and the like, with a boronic ester; neutralizing a reaction mixture by adding an acid; and then reacting the reaction mixture with a diol such as pinacol, thereby producing the compound (2a). When conducting the step [A-1], it can be done by referring to the reaction conditions, the post reaction treatment, and the purification method described in Production Examples 1 and 2 described later, and it is possible for a person with an ordinary skill in the art to easily decide optimal reaction conditions and the like.

In addition, the step [A-1] can also be conducted by adding an organometallic reagent to a mixture containing the compound (1a) and a boronic ester, thereby immediately after producing an anion from the compound (1a), the anion is reacted with the boronic ester.

The step [A-1] can also be conducted under the stream or the atmosphere of an inert gas such as nitrogen or argon.

As the compound (1a), chloroiodomethane, dibromomethane, bromoiodomethane, or the like can be used, for example. The compound (1a) is preferably chloroiodomethane or dibromomethane.

It is preferable to use a solvent in the step [A-1]. The solvent to be used in the step [A-1] is not particularly limited as long as it can dissolve starting materials to an extent and does not inhibit the reaction conducted in the step [A-1]. As the solvent, it is possible to use any solvent selected from the group consisting of an ether-based solvent such as tetrahydrofuran, 1,2-dimethoxyethane, methyl-t-butyl ether, cyclopentyl methyl ether, diethyl ether, diisopropyl ether, dibutyl ether, and dicyclopentyl ether; an aromatic hydrocarbon-based solvent such as benzene and toluene; an aliphatic hydrocarbon-based solvent such as heptane and hexane; and a mixed solvent thereof, for example. A particularly preferable solvent is tetrahydrofuran.

Examples of the abovementioned boronic ester include trimethyl borate and triisopropyl borate, although the boronic ester is not limited to these. A particularly preferable boronic ester is triisopropyl borate.

Examples of the abovementioned organometallic reagent include n-butyl lithium and s-butyl lithium, although the organometallic reagent is not limited to these. A particularly preferable organometallic reagent is n-butyl lithium.

Examples of the abovementioned acid, which is used to neutralize the reaction mixture, include methanesulfonic acid, p-toluenesulfonic acid, a hydrochloric acid-ethyl acetate solution, and a hydrochloric acid-methanol solution, although the acid is not limited to these. Particularly preferable acids are methanesulfonic acid and a hydrochloric acid-ethyl acetate solution.

A reaction time for the step [A-1] of the reaction scheme 1 usually varies depending on the types of starting materials used, a type of a solvent, a type of an organometallic reagent, a type of a boronic ester used, and a reaction temperature, and it is possible for a person with an ordinary skill in the art to easily select a preferable reaction time. For example, a mixture of an anionized compound, which is prepared by using the compound (1a) and an organic metal reagent at −78° C. (an outer temperature), and a boronic ester are stirred at a temperature described below for 1 to 3 hours. In addition, the obtained mixture is neutralized at a temperature described below, followed by adding a diol and stirring at a reaction temperature described below for 10 to 60 minutes.

[Reaction Temperature for the Reaction of a Compound, which is Prepared by Anionizing the Compound (1a), and a Boronic Ester]

A preferable reaction temperature for the reaction of a compound, which is prepared by anionizing the compound (1a), with a boronic ester varies depending on the types of starting materials used and the like as described above. However, this reaction is conducted preferably, while stirring, at 0° C. to room temperature (an outer temperature), and more preferably at room temperature.

[Reaction Temperature for the Neutralization Reaction and the Reaction with a Diol]

The reaction temperature during neutralizing a mixture obtained by the reaction of a compound, which is prepared by anionizing the compound (1a), and a boronic ester followed by adding a diol thereto is −20° C. to room temperature (an outer temperature), and more preferably 0° C. (outer temperature). The reaction temperature after adding a diol to a reaction mixture is 0° C. to room temperature (an outer temperature), and more preferably at room temperature.

[Used Amounts of an Organic Metal Reagent and a Boronic Ester]

The abovementioned organic metal reagent is used preferably at 0.8 to 1.2 moles, and more preferably at 0.8 to 1 mole, per 1 mole of the compound (1a).

A boronic ester is used preferably at 0.8 to 1.2 moles, and more preferably at 0.9 to 1 mole, per 1 mole of the compound (1a).

As described later in Example 22, the compound (2a) may be converted to another type of compound, in which Y is a different halogen atom, through a known halogen exchange reaction.

[Step [A-2]]

The step [A-2] is a step that includes: reacting an anionized compound, which is produced by the reaction of a compound (3a) and a base, and the compound (2a) in a solvent; and then reacting this reaction mixture with a hydrogen fluoride salt selected from potassium hydrogen fluoride and sodium hydrogen fluoride and the like, thereby producing the compound (I). More specifically, this step is conducted by referring to the reaction conditions, the post reaction treatment, and the purification method described in Examples 1, 3, 6, 8, 10, 12, 14, and 17 described later. In addition, it is possible for a person with an ordinary skill in the art to select appropriate reaction conditions and purification method depending on the types of used starting materials and the like.

In addition, the step [A-2] can also be conducted by adding a base to a mixture containing the compounds (2a) and (3a), thereby producing an anion from the compound (3a) and reacting the anion with the compound (2a).

The reactions in the step [A-2] can also be conducted under the stream or the atmosphere of an inert gas such as nitrogen or argon.

As the compound (3a), it is possible to use any compound selected from a commercially available compound, a known compound, and the compounds produced by using these compounds with a known method.

Examples of the abovementioned base to be reacted with the compound (3a) include sodium hydride, potassium bis(trimethylsilyl)amide, and potassium hydride, and sodium hydride and potassium bis(trimethylsilyl)amide are particularly preferable.

The solvent used in the step [A-2] is not particularly limited as long as it can dissolve starting materials used to an extent and does not inhibit the reaction. As the solvent, it is possible to use any solvent selected from the group consisting of an ether-based solvent such as tetrahydrofuran, 1,2-dimethoxyethane, methyl-t-butyl ether, cyclopentyl methyl ether, diethyl ether, diisopropyl ether, dibutyl ether, and dicyclopentyl ether; an aromatic hydrocarbon-based solvent such as benzene and toluene; an amide-based solvent such as N,N-dimethylformamide and N-methylpyrrolidinone; dimethylsulfoxide; and a mixed solvent thereof, for example. A particularly preferable solvent is tetrahydrofuran.

A reaction time for the step [A-2] varies depending on the types of used starting materials, a type of a used solvent, a type of a used reagent, and a reaction temperature, and it is possible for a person with an ordinary skill in the art to appropriately select a preferable reaction time. For example, the compound (3a) in the reaction scheme 1 is anionized by a base, and then stirred at a reaction temperature described below for 30 to 60 minutes. Next, the compound (2a) is added to the obtained mixture, followed by stirring at a reaction temperature described below for 1 to 12 hours. Moreover, a hydrogen fluoride salt is added to the obtained mixture, followed by stirring at a reaction temperature described below for 15 minutes to 12 hours.

[Reaction Temperature of the Reaction for Anionizing the Compound (3a) with a Base]

A reaction temperature of this reaction usually varies depending on the types of starting materials used, a type of a used solvent, and a type of a base used in the reaction, and it is possible for a person with an ordinary skill in the art to appropriately select a preferable reaction temperature. For example, the reaction temperature when adding a base to a solution containing the compound (3a) is preferably −78° C. to room temperature (an outer temperature), and more preferably 0° C. (an outer temperature).

The temperature after adding a base is preferably −78° C. to 70° C. (an outer temperature), and more preferably 0° C. to room temperature (an outer temperature).

[Reaction Temperature of the Reaction of a Compound, which is Prepared by Anionizing the Compound (3a), and a Compound (2a)]

A reaction temperature of this reaction usually varies depending on the types of starting materials used, a type of a used solvent, and a type of a reagent used in the reaction, and it is possible for a person with an ordinary skill in the art to appropriately select a preferable reaction temperature. For example, the reaction temperature when adding the compound (2a) to the reaction mixture is preferably 0° C. to room temperature (an outer temperature), and more preferably 0° C. (an outer temperature).

In addition, the reaction temperature after adding the compound (2a) is preferably 0° C. to 100° C. (an outer temperature), and more preferably room temperature to 70° C. (an outer temperature).

[Reaction Temperature of the Reaction in which a Hydrogen Fluoride Salt is Added]

As described above, the compound (3a) is anionized with a base, reacted by adding the compound (2a), and then reacted by further adding a hydrogen fluoride salt to the reaction mixture, thereby converting a boronic ester residue to a trifluoroborate group.

A reaction temperature of this reaction usually varies depending on the types of used starting materials, a type of a used solvent, and a type of a reagent used in the reaction, and it is possible for a person with an ordinary skill in the art to appropriately select a preferable reaction temperature. For example, the reaction temperature when adding a hydrogen fluoride salt to the reaction mixture is preferably 0° C. to room temperature (an outer temperature), and more preferably 0° C. (an outer temperature).

The reaction temperature after adding a hydrogen fluoride salt to the reaction mixture is preferably 0° C. to room temperature (an outer temperature), and more preferably at room temperature (an outer temperature).

[Used Amount of a Base]

The abovementioned base, which is used to anionize the compound (3a), is used preferably at 0.8 to 1.2 mole equivalent, and more preferably at 1 mole equivalent, per 1 mole of the compound (3a).

[Used Amounts of the Compounds (2a) and (3a)]

Also, in this reaction, the compound (3a) is used preferably at 1 to 10 mole equivalent, and more preferably at 1 to 3 mole equivalent, per 1 mole of the compound (2a).

[Used Amount of a Hydrogen Fluoride Salt]

The abovementioned hydrogen fluoride salt is used preferably at 2 to 8 mole equivalent, and more preferably at 2 to 5 mole equivalent, per 1 mole of the compound (2a).

[Preparation of a Tetraalkylammonium Salt and a Tetraalkylphosphonium Salt]

In the case where M in the compound (I) of the reaction scheme 1 is an alkali metal ion, this compound (I) can be further reacted with a reactant selected from tetraalkylammonium hydroxide, tetraalkylphosphonium hydroxide, and the like, thereby being converted into the compound (I), in which M represents $[N(R^1)(R^2)(R^3)(R^4)]^+$ or $[P(R^1)(R^2)(R^3)(4)]^+$ ($R^1$, $R^2$, $R^3$, and $R^4$ each independently represents a $C_{1-6}$ alkyl group or a $C_{7-16}$ aralkyl group). This step can be conducted by referring to the method described in Tetrahedron Letters, Vol. 42, pp. 9099-9103. Examples of the tetraalkylammonium hydroxide include tetarabutylammonium hydroxide. In addition, examples of the tetraalkylphosphonium hydroxide include tetrabutylphosphonium hydroxide.

As the solvent, which is used in the reaction to convert M from an alkali metal ion to a tetraalkylammonium salt or a tetraalkylphosphonium salt, a mixed solvent of dichloromethane or chloroform, and water can be used.

A reaction time of this salt exchange reaction is usually 1 to 30 minutes, and preferably 1 to 5 minutes, at room temperature (an outer temperature).

In addition, a reaction temperature of the salt exchange reaction is usually 10° C. to 50° C., and preferably room temperature (an outer temperature in each of the cases).

Also, various isomers obtained according to the compound (I) of the present invention (such as a geometric isomer, an optical isomer, a rotational isomer, a stereoisomer, and a tautomer) can be purified and isolated by using a conventional separation method such as recrystallization, a diastereomeric salt formation method, an enzymatic resolution, and various types of chromatography (such as thin layer chromatography, column chromatography, and gas chromatography).

[Intramolecular Alkoxymethylation Reaction Using a Fluoroboron Compound of the Present Invention or a Salt Thereof]

As described above, a compound (II) having a cyclic ether-fused aromatic ring can be obtained by the intramolecular alkoxymethylation reaction of the compound (I) of the present invention or the salt thereof in the presence of a metal catalyst. Hereinafter, this reaction will be described.

A scheme of a reaction in which the compound (II) is obtained from the compound (I) of the present invention is represented by the reaction scheme 2 below.

Reaction scheme 2

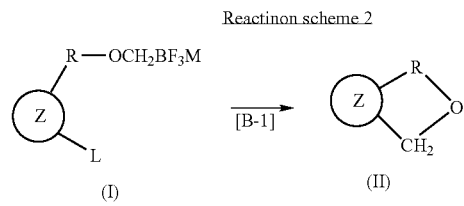

In the reaction scheme 2, the following moiety, L, R, and M represent the same as defined in the compound (I) described above.

[Step B-1]

The step [B-1] represented in the reaction scheme 2 is a step for producing the compound (II) from the compound (I) by the intramolecular alkoxymethylation reaction in an appropriate solvent.

This intramolecular alkoxymethylation reaction is conducted in the presence of a metal catalyst which is effective as a catalyst for this reaction. Examples of the metal catalyst include a metal such as a palladium metal, a platinum metal, a nickel metal, a rhodium metal, and an iridium metal; and a compound containing a metal selected from these metals. As the metal catalyst, a palladium metal is preferable. Specific examples of a palladium metal include palladium(II) acetate, tris(dibenzylideneacetone)dipalladium(0), palladium carbon, bis(triphenylphosphine)palladium(II) chloride, bis(tri-t-butylphosphine)palladium(0), tetrakis(triphenylphosphine) palladium(0), and 1,1'-bis(diphenylphosphino ferrocene) dichloropalladium(II). Of these, palladium(II) acetate, bis (tri-t-butylphosphine)palladium(0), tetrakis (triphenylphosphine)palladium(0), and 1,1'-bis (diphenylphosphino ferrocene)dichloropalladium(TI) are particularly preferable.

The abovementioned metal catalyst is used preferably at 0.001 to 0.5 mole equivalent, and more preferably at 0.02 to 0.2 mole equivalent, per 1 mole of the compound (1).

It is particularly preferable that the above intramolecular alkoxymethylation reaction be conducted in the presence of a base and a phosphine compound together with the abovementioned metal catalyst.

Examples of the above base include potassium phosphate tribasic, cesium carbonate, and cesium fluoride. Of these, potassium phosphate tribasic and cesium carbonate are preferable bases.

The above base is used preferably at 1 to 4 mole equivalent, and more preferably at 1.5 to 3 mole equivalent, per 1 mole of the compound (I) of the present invention.

Examples of the above phosphine compound include triphenylphosphine, tri-o-tolylphosphine, tri-t-butylphosphine, tricyclohexylphosphine, diphenylphosphinoferrocene, 2-dicyclohexylphosphino-2',6'-dimethoxybiphenyl, 2-dicyclohexylphosphino-2',4',6'-triisopropylbiphenyl, 2-di-t-butylphosphino-2',4',6'-triisopropylbiphenyl, 2-di-t-butylphosphinobiphenyl, 2-dicyclohexylphosphinobiphenyl, 2-dicyclohexylphosphino-2'-(N,N-dimethylamino)biphenyl, 2-di-t-butylphosphino-2'-(N,N-dimethylamino)biphenyl, 2,2-bis(diphenylphosphino)-1,1'-binaphthyl, 1,2-bis(diphenylphosphino)ethane, 1,3-bis(diphenylphosphino)propane, and 1,4-bis(diphenylphosphino)butane, and triphenylphosphine, tri-t-butylphosphine, diphenylphosphinoferrocene, and 2-dicyclohexylphosphino-2',6'-dimethoxybiphenyl are particularly preferable.

A phosphine compound is used preferably at 0.001 to 3 mole equivalent, and more preferably at 0.08 to 0.8 mole equivalent, per 1 mole of the compound (1).

When conducting the step [B-1], a solvent may be used, and the solvent is not particularly limited as long as it can dissolve starting materials to an extent and does not inhibit the reaction. Examples of the solvent, which can be used in the step [B-1], include an ether-based solvent such as tetrahydrofuran, 1,2-dimethoxyethane, methyl-t-butyl ether, cyclopentyl methyl ether, diethyl ether, diisopropyl ether, dibutyl ether, and dicyclopentyl ether; an aromatic hydrocarbon-based solvent such as benzene and toluene; an aliphatic hydrocarbon-based solvent such as heptane and hexane; an amide-based solvent such as N,N-dimethylformamide and N-methylpyrrolidinone; dimethylsulfoxide; water; and a mixed solvent thereof. A particularly preferable solvent is a mixed solvent of 1,4-dioxane and water.

Regarding specific details of the step [B-1] such as the reaction conditions, the post reaction treatment, and the purification method, by referring to the reaction conditions described in the following Examples 2, 4, 7, 9, 11, 13, 15, and 18, it is possible for a person with an ordinary skill in the art to easily decide optimal conditions for conducting the reaction, even when conducting an intramolecular alkoxymethylation reaction using the compound (I) with a chemical structure, which is different to those described in Examples.

A reaction temperature and a reaction time of the step [B-1] varies depending on the types of used starting materials, a type of a used solvent, a type of a reagent used in the reaction, and a reaction temperature, and it is possible for a person with an ordinary skill in the art to appropriately decide an optimal reaction temperature and an optimal reaction time. In general, a reaction temperature is preferably 50° C. to 150° C. (an outer temperature), and more preferably 95° C. to 140° C. (an outer temperature). In general, after mixing all starting materials, it is preferable that the reaction be conducted, while stirring, for 5 minutes to 72 hours, and more preferably 10 minutes to 24 hours.

This reaction can also be conducted under the stream or the atmosphere of an inert gas such as nitrogen or argon. In addition, this reaction can also be conducted by microwave irradiation, which is a known method for those skilled in the art.

EXAMPLES

The present invention will be described below in more detail on the basis of Examples. However, the present invention is not limited to these Examples.

In the following Examples, Production Examples 1 and 2 are examples of the step [A-1] of the abovementioned reaction scheme 1. Also, Examples 1, 3, 6, 8, 10, 12, 14, 17, 20, 26, and 28 are examples of the step [A-2] of the abovementioned reaction scheme 1. In addition, Examples 2, 4, 7, 9, 11, 13, 15, 18, 21, 27, and 29 are examples of the reaction represented in the above reaction scheme 2.

Moreover, in the following description, the term "an outer temperature", which represents a reaction temperature, refers to an outer temperature of a reaction vessel as described above.

Production Example 1

Synthesis of 2-(chloromethyl)-4,4,5,5-tetramethyl-1,3,2-dioxaborolane

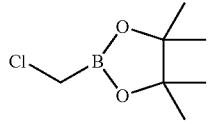

To the mixture of triisopropyl borate (15 ml, 65 mmol), chloroiodomethane (13 g, 72 mmol), and tetrahydrofuran (78 ml), n-butyllithium (a 1.6 M n-hexane solution, 41 ml, 65 mmol) was added dropwise at −78° C. (an outer temperature) over 20 minutes, and then the obtained mixture was stirred at room temperature for 2.5 hours. The reaction mixture was cooled to 0° C. (an outer temperature), and a 4 N hydrochloric acid-ethyl acetate solution was added dropwise thereto at the same temperature until the reaction mixture became neutral. At the same temperature, pinacol (7.7 g, 65 mmol) was added to the reaction mixture, and then the reaction mixture was stirred at room temperature for 40 minutes. The solvents were evaporated under reduced pressure, and then the obtained residue was distilled under reduced pressure (63-70° C., 11 mmHg), thereby obtaining the entitled compound (9.2 g, 52 mmol, 81%).

$^1$H-NMR Spectrum (CDCl$_3$) δ (ppm): 1.30 (12H, s), 2.97 (2H, s)

Production Example 2

Synthesis of 2-(bromomethyl)-4,4,5,5-tetramethyl-1,3,2-dioxaborolane

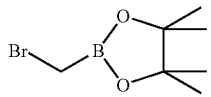

To the mixture of triisopropyl borate (20 g, 110 mmol), dibromomethane (8.6 ml, 120 mmol), and tetrahydrofuran (150 ml), n-butyllithium (a 2.6 M n-hexane solution, 39 ml, 100 mmol) was added dropwise at −78° C. (an outer temperature) over 1.5 hours, and then the reaction mixture was stirred at the same temperature for 1.5 hours. Subsequently, the obtained mixture was stirred at room temperature for 2 hours, and then was cooled to 0° C. (an outer temperature). To the reaction mixture, methanesulfonic acid (6.5 ml, 100 mmol) was added, and then the reaction mixture was stirred at room temperature for 1 hour. The obtained mixture was cooled to 0° C. (an outer temperature), pinacol (12 g, 100 mmol) was added to the reaction mixture, and then the reaction mixture was stirred at room temperature for 1 hour. The solvents were evaporated under reduced pressure from the reaction mixture, and then the obtained residue was distilled under reduced pressure (74-76° C., 8 mmHg), thereby obtaining the entitled compound (16 g, 72 mmol, 68%).

$^1$H-NMR Spectrum (CDCl$_3$) δ (ppm): 1.29 (12H, s), 2.59 (2H, s)

Example 1

Synthesis of sodium 2-chlorobenzyloxymethyl trifluoroborate

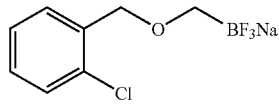

To the mixture of sodium hydride (61%, 150 mg, 3.8 mmol) and tetrahydrofuran (10 ml), 2-chlorobenzyl alcohol (590 mg, 4.2 mmol) was added at 0° C. (an outer temperature), and the obtained reaction mixture was stirred at room temperature for 30 minutes. To the reaction mixture, 2-(bromomethyl)-4,4,5,5-tetramethyl-1,3,2-dioxaborolane (92%, 500 mg, 2.1 mmol) synthesized in Production Example 2 was added at 0° C. (an outer temperature), and the obtained mixture was stirred at 30° C. (an outer temperature) overnight. After cooling the reaction mixture to 0° C. (an outer temperature), sodium hydrogen fluoride (580 mg, 9.4 mmol) was added to the reaction mixture at the same temperature, followed by the dropwise addition of water (8 ml) at the same temperature. After stirring the reaction mixture for 30 minutes at room temperature, the solvents were evaporated under reduced pressure. Acetone (40 ml) was added to the obtained residue, followed by filtration. The solvents were evaporated under reduced pressure from the filtrate, and then the obtained residue was washed with diethyl ether, thereby obtaining the entitled compound (280 mg, 55%).

$^1$H-NMR Spectrum (DMSO-d$_6$) δ (ppm): 2.65 (2H, q, J=5.3 Hz), 4.36 (2H, s), 7.24-7.28 (1H, m), 7.32 (1H, t, J=7.5 Hz), 7.38 (1H, d, J=7.7 Hz), 7.52 (1H, d, J=7.5 Hz)

Example 2

Synthesis of 1,3-dihydro-isobenzofuran

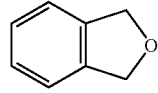

To the mixture of sodium 2-chlorobenzyloxymethyl trifluoroborate (40 mg, 0.16 mmol) synthesized in Example 1 and 1,4-dioxane (1.5 ml), water (0.15 ml), cesium carbonate (160 mg, 0.49 mmol), and bis(tri-t-butylphosphine)palladium(0) (8.3 mg, 0.016 mmol) were added at room temperature, and the obtained reaction mixture was then stirred at 100° C. (an outer temperature) overnight. The reaction mixture was cooled to room temperature, and then water and ethyl acetate were added thereto, followed by filtration with Celite. The organic layer of the filtrate was separated and washed with saturated saline. The solvents were evaporated under reduced pressure from the organic layer, and then the obtained residue was purified with silica gel column chromatography (hexane:diethyl ether=10:1), thereby obtaining the entitled compound (9.7 mg, 50%).

$^1$H-NMR Spectrum (CD$_3$OD) δ (ppm): 5.06 (4H, s), 7.26 (4H, s)

Example 3

Synthesis of sodium 2-(2-bromo-phenyl)-ethoxymethyl trifluoroborate

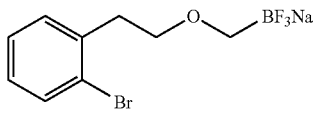

To the mixture of sodium hydride (61%, 130 mg, 3.3 mmol) and tetrahydrofuran (8 ml), 2-bromophenetyl alcohol (450 μl, 3.3 mmol) was added at 0° C. (an outer temperature), and the obtained reaction mixture was stirred at room temperature for 30 minutes. To the reaction mixture, 2-(bromomethyl)-4,4,5,5-tetramethyl-1,3,2-dioxaborolane (92%, 400 mg, 1.7 mmol) synthesized in Production Example 2 was added at 0° C. (an outer temperature), and the obtained mixture was stirred at room temperature overnight. After cooling the reaction mixture to 0° C. (an outer temperature), sodium hydrogen fluoride (460 mg, 7.5 mmol) was added to the reaction mixture at the same temperature, followed by the dropwise addition of water (8 ml) at the same temperature. After stirring the reaction mixture for 30 minutes at room temperature, the solvents were evaporated under reduced pressure. Acetone (15 ml) was added to the obtained residue, followed by filtration. The solvents were evaporated under reduced pressure from the filtrate, and then the obtained residue was washed with diethyl ether, thereby obtaining the entitled compound (260 mg, 51%).

$^1$H-NMR Spectrum (DMSO-d$_6$) δ (ppm): 2.54 (2H, q, J=5.5 Hz), 2.85-2.89 (2H, m), 3.36-3.40 (2H, m), 7.12-7.16 (1H, m), 7.28-7.32 (1H, m), 7.36-7.38 (1H, m), 7.55-7.57 (1H, m)

Example 4

Synthesis of Isochromane

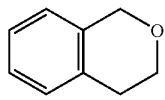

To the mixture of sodium 2-(2-bromo-phenyl)-ethoxymethyl trifluoroborate (50 mg, 0.16 mmol) synthesized in Example 3 and 1,4-dioxane (2 ml), water (0.2 ml), potassium phosphate tribasic (85%, 160 mg, 0.66 mmol), and tetrakis(triphenylphosphine)palladium(0) (38 mg, 0.033 mmol) were added at room temperature, and the obtained reaction mixture was then stirred at 100° C. (an outer temperature) overnight. The reaction mixture was cooled to room temperature, and then water and ethyl acetate were added thereto, followed by filtration with Celite. The organic layer of the filtrate was separated and washed with saturated saline. The solvents were evaporated under reduced pressure from the organic layer, and then the obtained residue was purified with silica gel column chromatography (heptane:ethyl acetate 10:1), thereby obtaining the entitled compound (1.3 mg, 6%).

$^1$H-NMR Spectrum (CDCl$_3$) δ (ppm): 2.87 (2H, t, J=5.7 Hz), 3.98 (2H, t, J=5.7 Hz), 4.78 (2H, d, J=0.4 Hz), 6.97-6.99 (1H, m), 7.10-7.18 (3H, m)

Example 5

Synthesis of (3-bromo-naphthalen-2-yl)-methanol

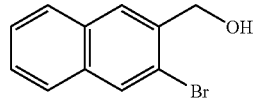

To the mixture of lithium aluminum hydride (430 mg, 9.0 mmol) and tetrahydrofuran (15 ml) under nitrogen atmosphere, aluminum chloride (1.7 g, 13 mmol) was added at 0° C. (an outer temperature), and the obtained reaction mixture was stirred at the same temperature for 1 hour. Subsequently, 3-bromo-naphthalene-2-carboxylic acid ethyl ester (500 mg, 1.8 mmol) was added to the reaction mixture at 0° C. (an outer temperature), and the reaction mixture was stirred at the same temperature for 1.5 hours. 28% ammonia water was added to the reaction mixture, followed by filtration with Celite. The solvents were evaporated under reduced pressure from the filtrate, and then the obtained residue was purified with NH-silica gel column chromatography (heptane:ethyl acetate=3:1), thereby obtaining the entitled compound (280 mg, 67%).

$^1$H-NMR Spectrum (DMSO-d$_6$) δ (ppm): 4.65 (2H, s), 5.57 (1H, t, J=5.6 Hz), 7.50-7.57 (2H, m), 7.88-7.92 (1H, m), 7.94-7.98 (1H, m), 8.03 (1H, s), 8.23 (1H, s)

Example 6

Synthesis of sodium (((3-bromo-2-naphthyl)methoxy)methyl)trifluoroborate

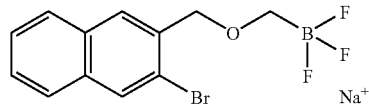

To the mixture of sodium hydride (50%, 61 mg, 1.3 mmol) and tetrahydrofuran (10 ml), (3-bromo-naphthalen-2-yl)-methanol (280 mg, 1.2 mmol) synthesized in Example 5 was added at 0° C. (an outer temperature), and the obtained reaction mixture was stirred at room temperature for 30 minutes. To the reaction mixture, a tetrahydrofuran (5 ml) solution of 2-(bromomethyl)-4,4,5,5-tetramethyl-1,3,2-dioxaborolane (92%, 130 mg, 0.60 mmol) synthesized in Production Example 2 was added at 0° C. (an outer temperature), and the obtained mixture was stirred at 60° C. (an outer temperature) for 1.5 hours. After cooling the reaction mixture to 0° C. (an outer temperature), sodium hydrogen fluoride (170 mg, 2.7 mmol) was added to the reaction mixture at the same temperature, followed by the dropwise addition of water (8 ml) at the same temperature. After stirring the reaction mixture overnight at room temperature, the solvents were evaporated under reduced pressure. Acetone (40 ml) was added to the obtained residue, and the resultant was heated, cooled to room temperature, and then was filtered. The solvents were evaporated under reduced pressure from the filtrate, and then the obtained residue was washed with diethyl ether, thereby obtaining the entitled compound (97 mg, 47%).

$^1$H-NMR Spectrum (CD$_3$OD) δ (ppm): 3.00 (2H, q, J=5.6 Hz), 4.66 (2H, s), 7.44-7.51 (2H, m), 7.75-7.78 (1H, m), 7.84-7.88 (1H, m), 8.05-8.09 (2H, m)

Example 7

Synthesis of 1,3-dihydronaphtho[2,3-c]furan

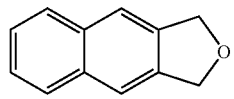

To the mixture of sodium (((3-bromo-2-naphthyl)methoxy)methyl)trifluoroborate (30 mg, 0.088 mmol) synthesized in Example 6 and 1,4-dioxane (1.0 ml), water (0.15 ml), cesium carbonate (86 mg, 0.26 mmol), 2-dicyclohexylphosphino-2',6'-dimethoxybiphenyl (7.2 mg, 0.018 mmol), palladium(II) acetate (2.0 mg, 0.009 mmol) were added at room temperature, and the obtained reaction mixture was then stirred at 100° C. (an outer temperature) for 16 hours. The reaction mixture was cooled to room temperature, and then water and dichloromethane were added thereto, followed by filtration with Celite. The organic layer of the filtrate was separated and washed with saturated saline. The solvents were evaporated under reduced pressure from the organic layer, and then the obtained residue was purified with silica gel column chromatography (hexane:ethyl acetate=10:1), thereby obtaining the entitled compound (10 mg, 67%).

$^1$H-NMR Spectrum (DMSO-d$_6$) δ (ppm): 5.13 (4H, s), 7.46-7.50 (2H, m), 7.80-7.83 (2H, m), 7.87-7.94 (2H, m)

Example 8

Synthesis of sodium (((2,4-dichlorobenzyl)oxy)methyl)trifluoroborate

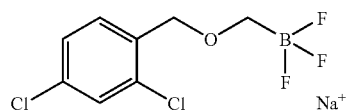

To the mixture of sodium hydride (50%, 130 mg, 2.6 mmol) and tetrahydrofuran (20 ml), 2,4-dichlorobenzyl alcohol (440 mg, 2.5 mmol) was added at 0° C. (an outer temperature), and the obtained reaction mixture was stirred at room temperature for 30 minutes. To the reaction mixture, a tetrahydrofuran (5 ml) solution of 2-(bromomethyl)-4,4,5,5-tetramethyl-1,3,2-dioxaborolane (92%, 300 mg, 1.3 mmol) synthesized in Production Example 2 was added at 0° C. (an outer temperature), and the obtained mixture was stirred at 60° C. (an outer temperature) for 1.5 hours. After cooling the reaction mixture to 0° C. (an outer temperature), sodium hydrogen fluoride (350 mg, 5.6 mmol) was added to the reaction mixture at the same temperature, followed by the dropwise addition of water (10 ml) at the same temperature.

After stirring the reaction mixture for 1 hour at room temperature, the solvents were evaporated under reduced pressure. Acetone (40 ml) was added to the obtained residue, and the resultant was heated, cooled to room temperature, and then was filtered. The solvents were evaporated under reduced pressure from the filtrate, and then the obtained residue was washed with diethyl ether, thereby obtaining the entitled compound (190 mg, 53%).

$^1$H-NMR Spectrum (CD$_3$OD) δ (ppm): 2.85-2.97 (2H, m), 4.52 (2H, s), 7.30 (1H, dd, J=2.4, 8.4 Hz), 7.39 (1H, d, J=2.0 Hz), 7.55-7.59 (1H, m)

Example 9

Synthesis of 5-chloro-1,3-dihydro-2-benzofuran

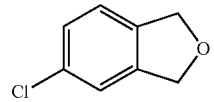

To the mixture of sodium (((2,4-dichlorobenzyl)oxy)methyl)trifluoroborate (50 mg, 0.18 mmol) synthesized in Example 8 and 1,4-dioxane (1.5 ml), water (0.15 ml), cesium carbonate (170 mg, 0.53 mmol), 2-dicyclohexylphosphino-2',6'-dimethoxybiphenyl (15 mg, 0.036 mmol), and palladium(II) acetate (4.0 mg, 0.018 mmol) were added at room temperature, and the obtained reaction mixture was then stirred at 100° C. (an outer temperature) for 8.5 hours. The reaction mixture was cooled to room temperature, and then water and dichloromethane were added thereto, followed by filtration with Celite. The organic layer of the filtrate was separated and washed with saturated saline. The solvents were evaporated under reduced pressure from the organic layer, and then the obtained residue was purified with silica gel column chromatography (hexane:ethyl acetate=10:1), thereby obtaining the entitled compound (1.1 mg, 4%).

$^1$H-NMR Spectrum (DMSO-d$_6$) δ (ppm): 4.98 (4H, s), 7.27-7.38 (2H, m), 7.38-7.44 (1H, m)

Example 10

Synthesis of sodium 2,6-dichlorobenzyloxymethyl trifluoroborate

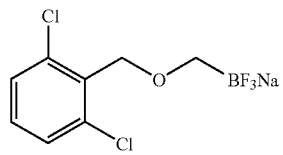

To the mixture of sodium hydride (61%, 180 mg, 4.5 mmol) and tetrahydrofuran (6 ml), 2,6-dichlorobenzyl alcohol (740 mg, 4.2 mmol) was added at 0° C. (an outer temperature), and the obtained reaction mixture was stirred at room temperature for 1 hour. To the reaction mixture, 2-(bromomethyl)-4,4,5,5-tetramethyl-1,3,2-dioxaborolane (92%, 500 mg, 2.1 mmol) synthesized in Production Example 2 and dissolved in tetrahydrofuran (4 ml) was added at 0° C. (an outer temperature), and the obtained mixture was stirred at 30° C. (an outer temperature) overnight. After cooling the reaction mixture to 0° C. (an outer temperature), sodium hydrogen fluoride (590 mg, 4.5 mmol) was added to the reaction mixture at the same temperature, followed by the dropwise addition of water (8 ml) at the same temperature. After stirring the reaction mixture for 30 minutes at room temperature, the solvents were evaporated under reduced pressure. Acetone (40 ml) was added to the obtained residue, followed by filtration. The solvents were evaporated under reduced pressure from the filtrate, and then the obtained residue was washed with diethyl ether, thereby obtaining the entitled compound (460 mg, 78%).

$^1$H-NMR Spectrum (DMSO-d$_6$) δ (ppm): 2.61 (2H, q, J=5.4 Hz), 4.46 (2H, s), 7.30-7.35 (1H, m), 7.44 (2H, d, J=8.0 Hz)

Example 11

Synthesis of 4-chloro-1,3-dihydro-isobenzofuran

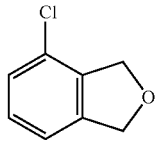

To the mixture of sodium 2,6-dichlorobenzyloxymethyl trifluoroborate (41 mg, 0.15 mmol) synthesized in Example 10 and 1,4-dioxane (1.5 ml), water (0.15 ml), cesium carbonate (170 mg, 0.51 mmol), palladium(II) acetate (3.3 mg, 0.015 mmol), and 2-dicyclohexylphosphino-2',6'-dimethoxybiphenyl (12 mg, 0.030 mmol) were added at room temperature, and the obtained reaction mixture was then stirred at 100° C. (an outer temperature) for 4 hours. The reaction mixture was cooled to room temperature, and then dichloromethane was added thereto. The organic layer was then separated and the solvents were evaporated under reduced pressure from the organic layer. The obtained residue was purified with silica gel column chromatography (hexane:diethyl ether=100:0→91:9→80:20), thereby obtaining the entitled compound (3.7 mg, 17%).

$^1$H-NMR Spectrum (CDCl$_3$) δ (ppm): 5.14 (2H, d, J=2.4 Hz), 5.17 (2H, d, J=2.0 Hz), 7.09-7.17 (1H, m), 7.20-7.24 (2H, m)

Example 12

Synthesis of sodium 2-chloro-4-fluorobenzyloxymethyl trifluoroborate

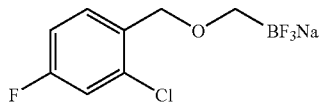

To the mixture of sodium hydride (66%, 150 mg, 4.2 mmol) and tetrahydrofuran (10 ml), 2-chloro-4-fluorobenzyl alcohol (99%, 680 mg, 4.2 mmol) was added at 0° C. (an outer temperature), and the obtained reaction mixture was stirred at room temperature for 1 hour. To the reaction mixture, 2-(bromomethyl)-4,4,5,5-tetramethyl-1,3,2-dioxaborolane (92%, 500 mg, 2.1 mmol) synthesized in Production Example 2 was added at 0° C. (an outer temperature), and the obtained mixture was stirred at 25 to 35° C. (an outer temperature) for 12 hours. After cooling the reaction mixture to 0° C. (an outer temperature), sodium hydrogen fluoride (97%, 600 mg, 9.4 mmol) was added to the reaction mixture at the same temperature, followed by the dropwise addition of water (12 ml) at the same temperature. After stirring the reaction mixture for 30 minutes at room temperature, the solvents were evaporated under reduced pressure. Acetone (40 ml) was added to the obtained residue, followed by filtration. The solvents were evaporated under reduced pressure from the filtrate, and then the obtained residue was washed with diethyl ether, thereby obtaining the entitled compound (300 mg, 55%).

$^1$H-NMR Spectrum (DMSO-d$_6$) δ (ppm): 2.65 (2H, q, J=6.5 Hz), 4.30 (2H, s), 7.18 (1H, ddd, J=3.5, 11.0, 11.0 Hz), 7.34 (1H, dd, J=3.5, 11.0 Hz), 7.48-7.53 (1H, m)

Example 13

Synthesis of 5-fluoro-1,3-dihydro-isobenzofuran

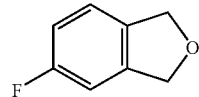

To the mixture of sodium 2-chloro-4-fluorobenzyloxymethyl trifluoroborate (300 mg, 1.2 mmol) synthesized in Example 12 and 1,4-dioxane (12 ml), water (1.2 ml), cesium carbonate (1.4 g, 4.0 mmol), palladium(II) acetate (27 mg, 0.12 mmol), and 2-dicyclohexylphosphino-2',6'-dimethoxybiphenyl (97 mg, 0.23 mmol) were added at room temperature, and the obtained reaction mixture was then stirred at 100° C. (an outer temperature) for 2 hours. The reaction mixture was cooled to room temperature, and then water and ethyl acetate were added thereto, followed by filtration using a filter paper. The organic layer of the filtrate was separated and washed with saturated saline. The solvents were evaporated under reduced pressure from the organic layer, and then the obtained residue was purified with silica gel column chromatography (heptane:ethyl acetate=10:1), thereby obtaining the entitled compound (41 mg, 26%).

$^1$H-NMR Spectrum (CDCl$_3$) δ (ppm): 5.06-5.10 (4H, m), 6.91-6.99 (2H, m), 7.17 (1H, dd, J=6.0, 10.0 Hz)

Example 14

Synthesis of sodium 2-chloro-5-nitrobenzyloxymethyl trifluoroborate

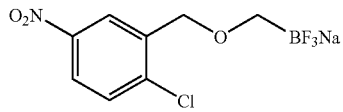

To the mixture of 2-(bromomethyl)-4,4,5,5-tetramethyl-1,3,2-dioxaborolane (92%, 700 mg, 2.9 mmol) synthesized in Production Example 2,2-chloro-5-nitrobenzyl alcohol (1.2 g, 6.4 mmol), and tetrahydrofuran (20 ml), sodium hydride (61%, 250 mg, 6.4 mmol) was added at 0° C. (an outer temperature), and the obtained reaction mixture was stirred at room temperature for 30 minutes. The reaction mixture was further stirred at 50° C. (an outer temperature) for 3 hours.

After cooling the reaction mixture to 0° C. (an outer temperature), sodium hydrogen fluoride (630 mg, 10 mmol) was added to the reaction mixture at the same temperature, followed by the dropwise addition of water (20 ml) at the same temperature. After stirring the reaction mixture for 15 minutes at room temperature, the solvents were evaporated under reduced pressure. Ethyl acetate (40 ml) was added to the obtained residue, followed by filtration. After evaporating the solvents from the filtrate under reduced pressure, the mixed solvent of ethyl acetate-diethyl ether (mainly ethyl acetate) was added to the obtained residue to solidify impurities, and the impurities were removed by filtration. After evaporating the solvents from the filtrate under reduced pressure, the obtained residue was recrystallized using the mixed solvent of ethyl acetate-diethyl ether (mainly diethyl ether), followed by filtration. The obtained crystals were washed with diethyl ether, thereby obtaining the entitled compound (140 mg, 17%).

$^1$H-NMR Spectrum (DMSO-$d_6$) δ (ppm): 2.72 (2H, q, J=5.3 Hz), 4.44 (2H, s), 7.71 (1H, d, J=8.8 Hz), 8.12 (1H, dd, J=2.9, 8.8 Hz), 8.32 (1H, d, J=2.9 Hz)

Example 15

Synthesis of 5-nitro-1,3-dihydro-isobenzofuran

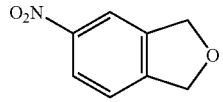

To the mixture of sodium 2-chloro-5-nitrobenzyloxymethyl trifluoroborate (30 mg, 0.10 mmol) synthesized in Example 14 and 1,4-dioxane (1.5 ml), water (0.15 ml), cesium carbonate (100 mg, 0.31 mmol), and bis(tri-t-butylphosphine)palladium(0) (11 mg, 0.021 mmol) were added at room temperature, and the obtained reaction mixture was then stirred at 100° C. (an outer temperature) overnight. The reaction mixture was cooled to room temperature, and then water and ethyl acetate were added thereto, followed by filtration with Celite. The organic layer of the filtrate was separated and washed with saturated saline. The solvents were evaporated under reduced pressure from the organic layer, and then the obtained residue was purified with silica gel column chromatography (heptane:ethyl acetate=6:1), thereby obtaining the entitled compound (9.9 mg, 58%).

$^1$H-NMR Spectrum (CDCl$_3$) δ (ppm): 5.18 (4H, s), 7.39 (1H, d, J=8.2 Hz), 8.11 (1H, d, J=2.0 Hz), 8.18 (1H, dd, J=2.0, 8.2 Hz)

Example 16

Synthesis of (2-chloro-6-methoxy-quinolin-3-yl)-methanol

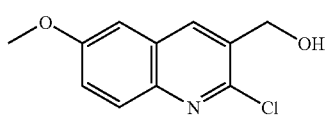

To the mixture of 2-chloro-6-methoxy-3-quinolinecarbaldehyde (3.1 g, 14 mmol) and methanol (10 ml), sodium borohydride (530 mg, 14 mmol) was added at 0° C. (an outer temperature), and the obtained reaction mixture was stirred at the same temperature for 30 minutes. Acetone was added to the reaction mixture at the same temperature, followed by the addition of water and ethyl acetate at the same temperature. The organic layer was separated and washed with saturated saline. The solvents were evaporated under reduced pressure from the organic layer, and then the obtained residue was purified with silica gel column chromatography (heptane: ethyl acetate=1:1), thereby obtaining the entitled compound (3.0 g, 98%).

$^1$H-NMR Spectrum (CDCl$_3$) δ (ppm): 2.16 (1H, t, J=5.9 Hz), 3.94 (3H, s), 4.92 (2H, d, J=5.9 Hz), 7.11 (1H, d, J=2.8 Hz), 7.37 (1H, dd, J=2.8, 9.2 Hz), 7.92 (1H, d, J=9.2 Hz), 8.19 (1H, s)

Example 17

Synthesis of sodium 2-chloro-6-methoxy-quinolin-3-ylmethoxymethyl trifluoroborate

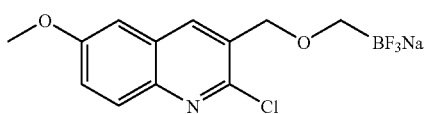

To the mixture of (2-chloro-6-methoxy-quinolin-3-yl)-methanol (1.4 g, 6.4 mmol) synthesized in Example 16 and tetrahydrofuran (50 ml), sodium hydride (61%, 250 mg, 6.4 mmol) was added at 0° C. (an outer temperature), and the obtained reaction mixture was stirred at room temperature for 20 minutes. To the reaction mixture, 2-(bromomethyl)-4,4,5,5-tetramethyl-1,3,2-dioxaborolane (92%, 700 mg, 2.9 mmol) synthesized in Production Example 2 was added at room temperature, and the obtained reaction mixture was stirred at 50° C. (an outer temperature) for 4 hours. After cooling the reaction mixture to 0° C. (an outer temperature), sodium hydrogen fluoride (630 mg, 10 mmol) was added to the reaction mixture at the same temperature, followed by the dropwise addition of water (40 ml) at the same temperature. After stirring the reaction mixture for 10 minutes at room temperature, the solvents were evaporated under reduced pressure. The obtained residue was washed with the mixed solvent of ethyl acetate-diethyl ether (1:4), thereby obtaining the entitled compound (610 mg, 64%).

$^1$H-NMR Spectrum (DMSO-$d_6$) δ (ppm): 2.75 (2H, q, J=5.3 Hz), 3.90 (3H, s), 4.48 (2H, s), 7.40 (1H, dd, J=2.9, 9.2 Hz), 7.45 (1H, d, J=2.7 Hz), 7.84 (1H, d, J=9.2 Hz), 8.32 (1H, s)

Example 18

Synthesis of 7-methoxy-1,3-dihydro-furo(3,4-b)quinoline

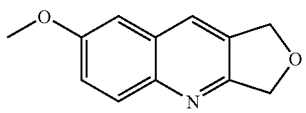

To the mixture of sodium 2-chloro-6-methoxy-quinolin-3-ylmethoxymethyl trifluoroborate (30 mg, 0.092 mmol) synthesized in Example 17 and 1,4-dioxane (1.0 ml), water (0.10 ml), cesium carbonate (90 mg, 0.28 mmol), and 1,1'-bis(diphenylphosphino) ferrocene dichloropalladium(II) (13 mg, 0.018 mmol) were added at room temperature, and the obtained reaction mixture was then stirred at 100° C. (an outer temperature) for 4 hours. The reaction mixture was cooled to room temperature, and then ethyl acetate was added thereto, followed by filtration with Celite. The solvents were evaporated under reduced pressure from the filtrate, and then the obtained residue was purified with silica gel column chromatography (hexane:ethyl acetate=1:1), thereby obtaining the entitled compound (5.1 mg, 28%).

$^1$H-NMR Spectrum (CDCl$_3$) δ (ppm): 3.94 (3H, s), 5.15 (2H, s), 5.28 (2H, s), 7.09 (1H, d, J=2.8 Hz), 7.36 (1H, dd, J=2.8, 9.2 Hz), 7.87 (1H, s), 7.95 (1H, d, J=9.2 Hz)

Example 19

Synthesis of 1-(2-bromo-phenyl)-ethanol

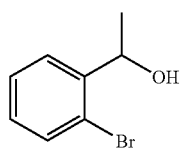

To the mixture of 2'-bromoacetophenone (3.9 g, 20 mmol) and methanol (50 ml), sodium borohydride (600 mg, 16 mmol) was added at 0° C. (an outer temperature), and the obtained reaction mixture was stirred at the same temperature for 30 minutes. Acetone was added to the reaction mixture at the same temperature, followed by the addition of water and ethyl acetate at the same temperature. The organic layer was separated and washed with saturated saline. The solvents were evaporated under reduced pressure from the organic layer, and then the obtained residue was filtered with NH-silica gel (heptane:ethyl acetate=1:1), thereby obtaining the entitled compound (3.9 g, 98%).

$^1$H-NMR Spectrum (CDCl$_3$) δ (ppm): 1.49 (3H, d, J=6.4 Hz), 1.95 (1H, d, J=3.7 Hz), 5.25 (1H, dq, J=3.5, 6.4 Hz), 7.11-7.15 (1H, m), 7.33-7.37 (1H, m), 7.51-7.53 (1H, m), 7.60 (1H, dd, J=1.7, 7.8 Hz)

Example 20

Synthesis of sodium 1-(2-bromo-phenyl)-ethoxymethyl trifluoroborate

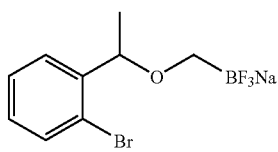

To the mixture of 1-(2-bromo-phenyl)-ethanol (1.0 g, 5.0 mmol) synthesized in Example 19 and tetrahydrofuran (20 ml), sodium hydride (61%, 200 mg, 5.0 mmol) was added at 0° C. (an outer temperature), and the obtained reaction mixture was stirred at 40° C. (an outer temperature) for 30 minutes. The reaction mixture was cooled to room temperature, followed by the addition of 2-(bromomethyl)-4,4,5,5-tetramethyl-1,3,2-dioxaborolane (92%, 480 mg, 2.0 mmol) thereto at the same temperature, and the reaction mixture was then stirred at 55° C. (an outer temperature) overnight. After cooling the reaction mixture to 0° C. (an outer temperature), sodium hydrogen fluoride (630 mg, 10 mmol) was added to the reaction mixture at the same temperature, followed by the dropwise addition of water (15 ml) at the same temperature. After stirring the reaction mixture for 15 minutes at room temperature, the solvents were evaporated under reduced pressure. To the obtained residue, the mixed solvent (30 ml) of acetone-methanol (99:1) was added, followed by filtration, and the solvents were evaporated under reduced pressure from the filtrate. The obtained residue was washed with diethyl ether, thereby obtaining the entitled compound (470 mg, 78%).

$^1$H-NMR Spectrum (DMSO-d$_6$) δ (ppm): 1.21 (3H, d, J=6.4 Hz), 2.36 (2H, q, J=5.5 Hz), 4.42 (1H, q, J=6.4 Hz), 7.13-7.17 (1H, m), 7.35-7.39 (1H, m), 7.47 (1H, dd, J=1.8, 7.7 Hz), 7.50-7.52 (1H, m)

Example 21

Synthesis of 1-methyl-1,3-dihydro-isobenzofuran

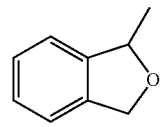

The mixture of sodium 1-(2-bromo-phenyl)-ethoxymethyl trifluoroborate (30 mg, 0.092 mmol) synthesized in Example 20, tetrakis(triphenylphosphine)palladium(0) (13 mg, 0.018 mmol), cesium carbonate (90 mg, 0.28 mmol), 1,4-dioxane (1.0 ml), and water (0.10 ml) was stirred at 135° C. for 90 minutes under microwave irradiation. The reaction mixture was cooled to room temperature, and then water and heptane were added thereto, followed by filtration with Celite. The organic layer of the filtrate was separated and washed with saturated saline. The solvents were evaporated under reduced pressure from the organic layer, and then the obtained residue was purified with silica gel column chromatography (hexane alone→hexane:diethyl ether=30:1), thereby obtaining the entitled compound (35.7 mg, 41%).

$^1$H-NMR Spectrum (CDCl$_3$) δ (ppm): 1.50 (3H, dd, J=0.6, 6.3 Hz), 5.03-5.06 (1H, m), 5.14 (1H, dd, J=2.5, 12.2 Hz), 5.30-5.35 (1H, m), 7.15-7.17 (1H, m), 7.21-7.28 (3H, m)

Example 22

Synthesis of 2-(iodomethyl)-4,4,5,5-tetramethyl-1,3,2-dioxaborolane

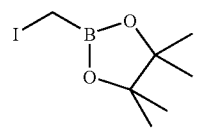

To the mixture of 2-(bromomethyl)-4,4,5,5-tetramethyl-1,3,2-dioxaborolane (2.0 g, 8.3 mmol) synthesized in Production Example 2 and acetone (17 ml), sodium iodide (1.9 g, 13 mmol) was added at room temperature, and the obtained reaction mixture was stirred at room temperature for 2 hours. Impurities were removed by filtration, and the solvents were evaporated under reduced pressure from the filtrate. Hexane was added to the obtained residue, and insoluble matter was removed by filtration. The solvents were evaporated under reduced pressure from the filtrate, thereby obtaining the entitled compound (2.2 g, 97%).

$^1$H-NMR Spectrum (CDCl$_3$) δ (ppm): 1.29 (12H, s), 2.59 (2H, s)

Example 23

Synthesis of 2,6-dichloro-nicotinic acid methyl ester

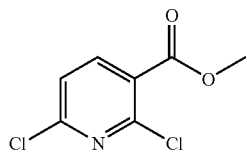

To the mixture of 2,6-dichloro-nicotinic acid (4.7 g, 22 mmol) and acetone (22 ml), potassium carbonate (4.6 g, 33 mmol) and dimethylsulfate (2.4 ml, 24 mmol) were sequentially added at room temperature, and the obtained reaction mixture was stirred at room temperature for 16 hours. Impurities were removed by filtration, and the solvents were evaporated under reduced pressure from the filtrate. Dichloromethane was added to the obtained residue, followed by washing with a saturated sodium bicarbonate aqueous solution. The obtained organic layer was dried using anhydrous sodium sulfate, and the solvents were evaporated under reduced pressure. The obtained residue was purified with silica gel column chromatography (heptane:ethyl acetate=10:1 to 1:1), thereby obtaining the entitled compound (4.0 g, 87%).

$^1$H-NMR Spectrum (CDCl$_3$) δ (ppm): 3.96 (3H, s), 7.36 (1H, d, J=8.0 Hz), 8.16 (1H, d, J=8.0 Hz)

Example 24

Synthesis of 2-chloro-6-phenyl-nicotinic acid methyl ester

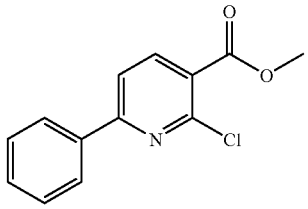

To the mixture of 2,6-dichloro-nicotinic acid methyl ester (4.0 g, 19 mmol) synthesized in Example 23 and tetrahydrofuran (39 ml), phenyl boronic acid (2.5 g, 19 mmol), potassium carbonate (8.0 g, 58 mmol), and tetrakis(triphenylphosphine)palladium(0) (1.2 g, 0.97 mmol) were added, and the obtained reaction mixture was stirred for 16 hours while being heated to reflux. The reaction mixture was cooled to room temperature, and then insoluble matter was removed by filtration. The solvents were evaporated under reduced pressure from the filtrate, and then water and ethyl acetate were added to the obtained residue, followed by extraction. The organic layer and the aqueous layer were separated, and the aqueous layer was further extracted using ethyl acetate. The organic layers were mixed, washed with saturated saline, and dried using anhydrous sodium sulfate. The solvents were evaporated under reduced pressure, and the obtained residue was purified with silica gel column chromatography (heptane:ethyl acetate=10:1 to 3:1). The obtained crude compound was recrystallized using the mixed solvent of heptane-diethyl ether, thereby obtaining the entitled compound (2.2 g, 47%).

$^1$H-NMR Spectrum (CDCl$_3$) δ (ppm): 3.98 (3H, s), 7.46-7.53 (3H, m), 7.74 (1H, d, J=8.0 Hz), 8.04-8.08 (2H, m), 8.25 (1H, d, J=8.0 Hz)

Example 25

Synthesis of (2-chloro-6-phenyl-pyridin-3-yl)-methanol

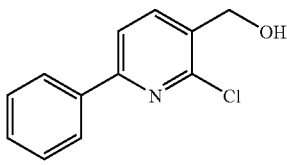

To the mixture of lithium aluminum hydride (120 mg, 2.5 mmol) and tetrahydrofuran (10 ml), a mixture of 2-chloro-6-phenyl-nicotinic acid methyl ester (620 mg, 2.5 mmol) synthesized in Example 24 and tetrahydrofuran (2.4 ml) was gradually added under nitrogen atmosphere at 0° C. (an outer temperature), and the obtained reaction mixture was stirred at the same temperature for 30 minutes. Water was gradually added dropwise thereto at the same temperature, and the obtained reaction mixture was stirred at room temperature for 1 hour. Impurities were removed by filtration with Celite, and the solvents were evaporated under reduced pressure from the filtrate. The obtained residue was purified with silica gel column chromatography (heptane:ethyl acetate=2:1), thereby obtaining the entitled compound (470 mg, 86%).

$^1$H-NMR Spectrum (CDCl$_3$) δ (ppm): 2.00 (1H, t, J=6.0 Hz), 4.83 (2H, d, J=6.0 Hz), 7.40-7.52 (3H, m), 7.71 (1H, d, J=8.0 Hz), 7.92 (1H, d, J=8.0 Hz), 8.00 (2H, d, J=6.8 Hz)

Example 26

Synthesis of sodium (2-chloro-6-phenyl-pyridin-3-yl)-methoxymethyl trifluoroborate

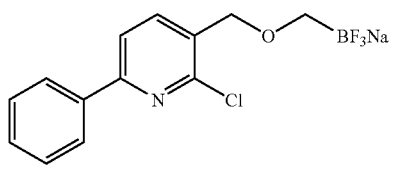

To the mixture of sodium hydride (61%, 84 mg, 2.1 mmol) and tetrahydrofuran (6 ml), (2-chloro-6-phenyl-pyridin-3-yl)-methanol (470 mg, 2.1 mmol) synthesized in Example 25 was added at 0° C. (an outer temperature), and the obtained reaction mixture was stirred at room temperature for 1 hour. To the reaction mixture, 2-(iodomethyl)-4,4,5,5-tetramethyl-1,3,2-dioxaborolane (260 mg, 0.97 mmol) synthesized in Example 22 was added at 0° C. (an outer temperature), and the obtained reaction mixture was stirred at room temperature for 14 hours. To the reaction mixture, sodium bifluoride (97%, 250 mg, 3.9 mmol) was added at 0° C. (an outer temperature), followed by the dropwise addition of water (12 ml) at the same temperature. After stirring the reaction mixture for 30 minutes at room temperature, the solvents were evaporated under reduced pressure. To the obtained residue, an excessive amount of acetone was added, followed by filtration, and the solvents were evaporated under reduced pressure from the filtrate. Diethyl ether was added to the obtained residue, followed by filtration. The solids precipitated in the filtrate were collected, thereby obtaining the entitled compound (36 mg, 12%).

$^1$H-NMR Spectrum (DMSO-$d_6$) δ (ppm): 2.63-2.69 (2H, m), 4.37 (2H, s), 7.42-7.52 (3H, m), 7.96 (1H, d, J=8.0 Hz), 8.00 (1H, d, J=8.0 Hz), 8.02-8.06 (2H, m)

Example 27

Synthesis of
2-phenyl-5,7-dihydro-furo[3,4-b]pyridine

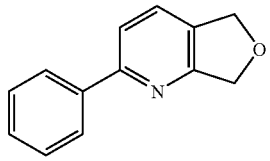

To the mixture of sodium (2-chloro-6-phenyl-pyridin-3-yl)-methoxymethyl trifluoroborate (36 mg, 0.111 mmol) synthesized in Example 26 and 1,4-dioxane (1 ml), water (0.1 ml), cesium carbonate (114 mg, 0.333 mmol), and tetrakis (triphenylphosphine)palladium(0) (26 mg, 0.022 mmol) were added at room temperature, and the obtained reaction mixture was stirred at 140° C. for 15 minutes under microwave irradiation. The reaction mixture was cooled to room temperature, and then water and ethyl acetate were added thereto, and the obtained organic layer was washed with saturated saline. The solvents were evaporated under reduced pressure from the organic layer, and then the obtained residue was purified with silica gel column chromatography (heptane ethyl acetate=5:1), thereby obtaining the entitled compound (1.1 mg, 5%).

$^1$H-NMR Spectrum (CDCl$_3$) δ (ppm): 5.14 (2H, s), 5.21 (2H, s), 7.39-7.51 (3H, m), 7.59-7.64 (2H, m), 7.94-7.98 (2H, m)

Example 28

Synthesis of sodium
2-chloro-6-methoxy-quinolin-3-ylmethoxymethyl
trifluoroborate (Alternative method for synthesizing 7-methoxy-1,3-dihydro-furo(3,4-b)quinoline described in Example 18)

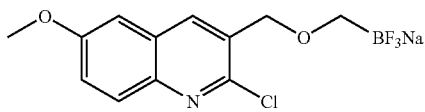

To the mixture of sodium hydride (61%, 250 mg, 6.4 mmol) and tetrahydrofuran (25 ml), (2-chloro-6-methoxy-quinolin-3-yl)-methanol (1.4 g, 6.4 mmol) synthesized in Example 16 was added at 0° C. (an outer temperature), and the obtained reaction mixture was stirred at room temperature for 40 minutes. To the reaction mixture, 2-(bromomethyl)-4,4,5,5-tetramethyl-1,3,2-dioxaborolane (92%, 700 mg, 2.9 mmol) synthesized in Production Example 2 was added at 0° C. (an outer temperature), and the obtained reaction mixture was stirred at 50° C. (an outer temperature) for 5 hours. After cooling the reaction mixture to 0° C. (an outer temperature), sodium hydrogen fluoride (580 mg, 9.3 mmol) was added to the reaction mixture at the same temperature, followed by the dropwise addition of water (20 ml) at the same temperature. After stirring the reaction mixture for 15 minutes at room temperature, the solvents were evaporated under reduced pressure. Acetone was added to the obtained residue, followed by filtration, and the solvents were evaporated under reduced pressure from the filtrate. Ethyl acetate was then added to the obtained residue, followed by filtration, and the solvents were evaporated under reduced pressure from the filtrate. The mixed solvent of ethyl acetate-diethyl ether (1:4) was added to the obtained residue, followed by filtration. The crystals precipitated in the filtrate were collected, thereby obtaining the entitled compound (260 mg). The solvents were evaporated under reduced pressure from the filtrate, and ethyl acetate was added to the obtained residue and then heated to 60° C., resulting in the precipitation of crystals. The crystals were collected, thereby obtaining the entitled compound (250 mg (510 mg in total), 53%).

$^1$H-NMR Spectrum (DMSO-$d_6$) δ (ppm): 2.75 (2H, q, J=5.3 Hz), 3.90 (3H, s), 4.47 (2H, s), 7.40 (1H, dd, J=2.9, 9.2 Hz), 7.46 (1H, d, J=2.7 Hz), 7.84 (1H, d, J=9.2 Hz), 8.32 (1H, s)

Example 29

Synthesis of
7-methoxy-1,3-dihydro-furo[3,4-b]quinoline

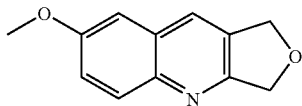

To the mixture of sodium 2-chloro-6-methoxy-quinolin-3-ylmethoxymethyl trifluoroborate (100 mg, 0.31 mmol) synthesized in Example 28 and 1,4-dioxane (3 ml), water (0.3 ml), cesium carbonate (310 mg, 0.92 mmol), and tetrakis (triphenylphosphine)palladium(0) (73 mg, 0.061 mmol) were added at room temperature, and the obtained reaction mixture was stirred at 140° C. for 10 minutes under microwave irradiation. The reaction mixture was cooled to room temperature, and then water and ethyl acetate were added thereto, and the obtained organic layer was washed with saturated saline. The solvents were evaporated under reduced pressure from the organic layer, and then the obtained residue was purified with silica gel column chromatography (heptane: ethyl acetate=2:1), thereby obtaining the entitled compound (44 mg, 71%).

$^1$H-NMR Spectrum (CDCl$_3$) δ (ppm): 3.94 (3H, s), 5.15 (2H, s), 5.28 (2H, s), 7.09 (1H, d, J=2.8 Hz), 7.36 (1H, dd, J=2.8, 9.2 Hz), 7.87 (1H, s), 7.95 (1H, d, J=9.2 Hz)

INDUSTRIAL APPLICABILITY

By using the fluoroboron compound of the present invention or the salt thereof and conducting an intramolecular alkoxymethylation reaction in the presence of a metal catalyst, a compound having a cyclic ether-fused aromatic ring can be produced by one-step reaction.

What is claimed is:

1. A fluoroboron compound or a salt thereof,
   wherein said fluoroboron compound or the salt thereof is capable of forming a cyclic ether fused with an aromatic ring by an intramolecular alkoxymethylation reaction,
   wherein said fluoroboron compound is represented by the following formula (I):

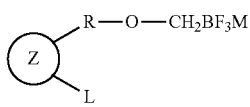
(I)

(wherein the moiety represented by the formula

represents an aromatic ring which may or may not have substituents other than L and —R—O—CH$_2$BF$_3$M groups, wherein said aromatic ring is selected from the group consisting of benzene, naphthalene, pyridine and quinoline; L represents a leaving group selected from the group consisting of a halogen atom, a substituted alkylsulfonyloxy group, an unsubstituted alkylsulfonyloxy group, a substituted arylsulfonyloxy group and an unsubstituted arylsulfonyloxy group; R represents a substituted or unsubstituted alkylene group of 1 or 2 carbon atoms; M represents an alkali metal cation, [N(R$^1$)(R$^2$)(R$^3$)(R$^4$)]$^+$, or [P(R$^1$)(R$^2$)(R$^3$)(R$^4$)]$^+$, (in which R$^1$, R$^2$, R$^3$, and R$^4$ each independently represents a C$_{1-6}$ alkyl group or a C$_{7-16}$ aralkyl group); with the proviso that L and —R—OCH$_2$BF$_3$M are respectively located on contiguous carbon atoms on the aromatic ring or, in the case where the aromatic ring is a fused aromatic ring formed of 2 rings, on two carbon atoms adjacent to one carbon at the fused position.

2. The fluoroboron compound or the salt thereof according to claim 1, wherein said leaving group L is a halogen atom.

3. The fluoroboron compound or the salt thereof according to claim 1 or 2,
   wherein said R represents a methylene group or an ethylene group which may optionally be substituted by one or more C$_{1-6}$ alkyl groups.

4. The fluoroboron compound or the salt thereof according to claim 1,
   wherein said aromatic ring represented by the following formula

is selected from the group consisting of a benzene ring and a naphthalene ring.

5. The fluoroboron compound or the salt thereof according to claim 1,
   wherein said aromatic ring represented by the following formula

is selected from the group consisting of a pyridine ring, and a quinoline ring.

6. The fluoroboron compound or the salt thereof according to claim 1,
   wherein said aromatic ring represented by the following formula

is a benzene ring, a quinoline ring, or a naphthalene ring.

7. The fluoroboron compound or the salt thereof according to claim 1, wherein said M is an alkali metal cation.

8. The fluoroboron compound or the salt thereof according to claim 7, wherein said M is a potassium ion or a sodium ion.

9. A method for producing a compound represented by the following formula (II) and having a cyclic ether-fused aromatic ring, the method comprising a step of:
   causing an intramolecular alkoxymethylation reaction of the fluoroboron compound or the salt thereof of claim 2 in the presence of a metal catalyst

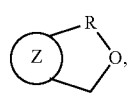
(II)

wherein Z is selected from the group consisting of a benzene ring, a naphthalene ring, a pyridine ring, and a quinoline ring; and
R represents a substituted or unsubstituted alkylene group of 1 or 2 carbon atoms.

* * * * *